(12) United States Patent
Abedin-Nasab

(10) Patent No.: US 11,185,376 B2
(45) Date of Patent: Nov. 30, 2021

(54) ROBOT FOR PLACEMENT OF SPINAL INSTRUMENTATION

(71) Applicant: Rowan University, Glassboro, NJ (US)

(72) Inventor: Mohammad Hossein Abedin-Nasab, Swedesboro, NJ (US)

(73) Assignee: ROWAN UNIVERSITY, Glassboro, NJ (US)

( * ) Notice: Subject to any disclaimer, the term of this patent is extended or adjusted under 35 U.S.C. 154(b) by 287 days.

(21) Appl. No.: 16/374,024

(22) Filed: Apr. 3, 2019

(65) Prior Publication Data

US 2019/0357985 A1    Nov. 28, 2019

Related U.S. Application Data

(60) Provisional application No. 62/654,708, filed on Apr. 9, 2018.

(51) Int. Cl.

| A61B 34/20 | (2016.01) |
| A61B 34/30 | (2016.01) |
| A61B 34/10 | (2016.01) |
| A61B 34/00 | (2016.01) |
| A61B 90/11 | (2016.01) |
| A61B 90/00 | (2016.01) |

(52) U.S. Cl.
CPC .............. *A61B 34/20* (2016.02); *A61B 34/10* (2016.02); *A61B 34/25* (2016.02); *A61B 34/30* (2016.02); *A61B 90/11* (2016.02); *A61B 90/361* (2016.02); *A61B 90/37* (2016.02); *A61B 2034/107* (2016.02); *A61B 2034/2051* (2016.02); *A61B 2034/2055* (2016.02); *A61B 2090/364* (2016.02)

(58) Field of Classification Search
CPC ......... A61B 34/10; A61B 34/30; A61B 34/76; A61B 2034/104; A61B 2034/303; A61B 2034/305
See application file for complete search history.

(56) References Cited

U.S. PATENT DOCUMENTS

| 5,533,418 A * | 7/1996 | Wu .......................... B25J 9/102 |
| | | 248/181.1 |
| 7,789,874 B2 * | 9/2010 | Yu ........................... A61B 90/50 |
| | | 606/1 |
| 8,682,489 B2 * | 3/2014 | Itkowitz ................ B25J 9/1689 |
| | | 700/258 |
| 8,968,333 B2 * | 3/2015 | Yu ........................... A61B 90/50 |
| | | 606/130 |
| 9,027,441 B2 * | 5/2015 | Gewirtz ................ F16H 37/065 |

(Continued)

*Primary Examiner* — Anu Ramana
(74) *Attorney, Agent, or Firm* — Domingos J. Silva; Paul A. Leicht; Saul Ewing Arnstein & Lehr LLP

(57) ABSTRACT

A robot for spinal surgery may include an open rectangular base designed to slide on a rail of a fixed support to reach to different parts of the spine. The robot may include a moving top platform that can accommodate a surgical instrument, and three legs to support the top platform on the base and move the top platform in 6-degree-of-freedom relative to the base. In one embodiment, each of the three legs may include a lower part and an upper part joined by an electric linear actuator for sliding the upper part linearly relative to the lower part. In one embodiment, the lower part of each leg may be joined to a shaft of a rotary actuator that is mounted to the base, and the upper part of each log can be joined to the top platform at a fixed point via a passive spherical joint.

16 Claims, 7 Drawing Sheets

(56) References Cited

U.S. PATENT DOCUMENTS

| | | | |
|---|---|---|---|
| 9,603,672 B2 * | 3/2017 | Shellenberger | A61B 34/30 |
| 10,368,954 B2 * | 8/2019 | Brisson | A61B 34/30 |
| 10,390,898 B2 * | 8/2019 | Jensen | F16H 55/0813 |
| 2009/0024141 A1 * | 1/2009 | Stahler | A61B 34/37 606/130 |
| 2009/0138025 A1 * | 5/2009 | Stahler | A61B 34/30 606/130 |

* cited by examiner

ROBOT FOR PLACEMENT OF SPINAL INSTRUMENTATION

CROSS-REFERENCE TO RELATED APPLICATION

This application claims the benefit of priority under 35 U.S.C. § 119(e) to U.S. Provisional Patent Application Ser. No. 62/654,708, filed Apr. 9, 2018. The entire content of this application is hereby incorporated by reference herein.

BACKGROUND

Spinal surgery requires a very high level of precision, as it has considerable risks due to the critical structures that surround the spinal column. Damage to any of these structures can produce considerable side effects, ranging from pain to paralysis. For example, In addition to the blunt trauma and penetrating trauma that is common in many communities, along the Jersey Shore, there is an exceedingly high rate of aquatic spinal cord injuries and approximately 50% of aquatic spinal fractures have a spinal injury. The presence of significant bony displacement that compresses the spinal cord is a particular challenge in the care of these spinal injuries.

Even though still at an early stage of development, the robot system has the potential to ease placement of instrumentation and speed the surgery. Many variations of 6-legged parallel device, such as the Gough-Stewart platform 100 as shown in FIG. 1, have been proposed to optimize the performance of the robotic manipulators for non-medical applications, for example, using as a telescope stand. However, these systems tend to be complex and imposing limitations to applications in the medical field.

The present invention is designed to address these shortcomings for the field of medical robot systems.

SUMMARY

Various embodiments for a robot for placement of spinal instrumentation are described. In one embodiment, a robot for use in a spinal surgery may include an open rectangular base having at least three sides, of which the longest side may slide on a rail of a fixed support. The robot may include a moving top platform that includes a portion of a circle having two ends, a cross bar connecting the two ends, and a guide attached to the cross bar and designed to attach a surgical instrument thereon. The robot may have three legs to support the top platform on the base and move the top platform in 6-degree-of-freedom relative to the base. In one embodiment, each of the three legs may include a lower part and an upper part rotatably joined by an electric linear actuator, the linear actuator being used to slide the upper part linearly relative to the lower part. In one embodiment, the lower part and upper part of the leg are part of the electric liner actuator. In another embodiment, the lower or upper part of the leg may be separate and joined to the linear actuator.

The legs between the top platform and the base may be joined by various joints. For example, the lower part of each leg may be joined to a shaft of a rotary actuator through a passive resolute joint, where the rotary actuator is mounted on the base at a fixed point and the shaft of the rotatory can rotate relative to the base. In one embodiment, the upper part of each log can be joined to the top platform at a fixed point via a passive spherical joint. The top platform can be equipped with a guide, such as a hollow cylinder, for accommodating a surgical instrument.

During a surgery, the robot may be mounted to a tracking system of a fixed support and slide along a rail of the tracking system for a surgeon to work on different parts of the patient. In one embodiment, the robot may also mount a movable housing thereon for accommodating an imaging probe such as an ultrasound imaging device. The system may capture one or more images of the patient and construct a 3D imaging for the surgeon to analyze specific part of the patient.

In one embodiment, a method using the robot system in a spinal surgery may include controlling of the robot system to move a surgical equipment to a desired location. The method may include receiving a trajectory position instruction, whether from a user via a graphical user interface, a pointing device such as a joystick, or from another robot such as a master robot. The method may include converting the trajectory position instructions to one or more control parameters for each of the three rotary actuators and three linear actuators, and operating the actuators based on the control parameters.

In one embodiment, the robot may function as a slave robot, which receive trajectory position instructions from a master robot, and operate its actuators based on the instructions from the master robot but with higher precision and force. Alternatively and/or additionally, the robot may operate based on a path planning developed in a preoperative planning process. Additionally, the method for controlling the robot movement may include receiving a position feedback and adjusting the robot position based on the feedback.

DETAILED DESCRIPTION

Figure 1:
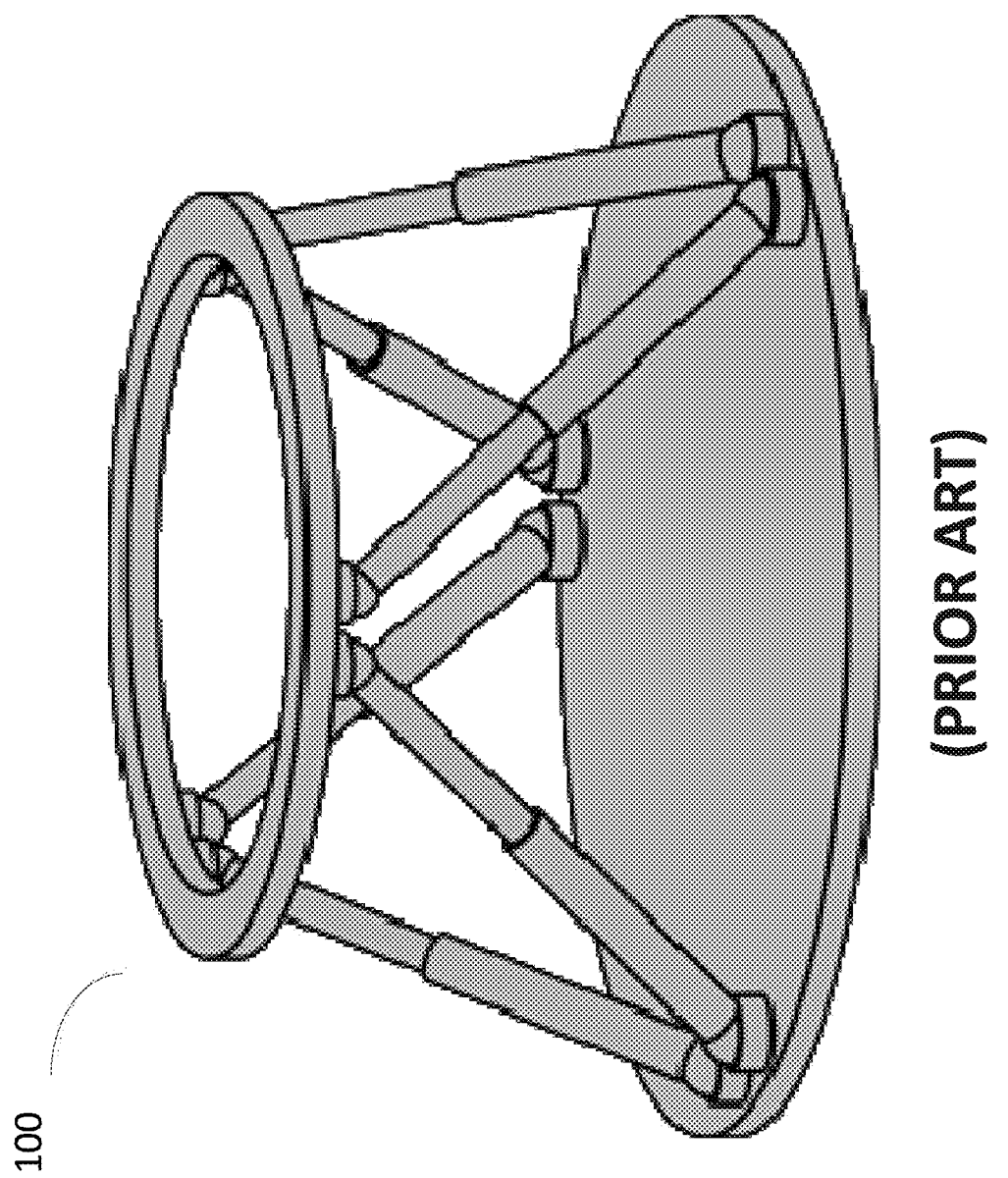
FIG. 1 illustrates an example of prior art robot system using 6 legs.

There are several potential advantages of the robotic technology in the care of spinal cord injury patients. For example, in long bone fractures robotic screws can be placed percutaneously. As such, at least one aspect of the present invention may include reducing exposure to the entire spine structure. Less exposure will reduce the duration of surgery and the likelihood of postoperative infection. Further, in another aspect, the instantly described robot system allows surgeon to place the pins and other repairing devices at a much quicker time window. Even further, the system allows more precise placement of such devices than an open surgery can permit.

In another aspect, the system limits radiation exposure to the medical staff during a given procedure. Additionally, the needed force during the surgery can be applied more precisely than if performed by a human hand. As such, the system described herein subjects the patient to less potential over or under-manipulation which can complicate clinical outcome. In another aspect, the present invention provides accurate preoperative planning by the medical staff based on patient's medical needs, thereby reducing unnecessary maneuvering of the patient during the surgery.

In at least one embodiment the robot system of the present invention can be attached to the patient through a support frame. With a user-friendly computer graphic interface, the surgeon can easily plan for the operation and can define the exact screw positions, adjust the rod lengths, number and size of the screws, and make these adjustments in different axial or sagittal planes while making sure the spinal canal is not violated.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

The term "leg" as used herein refers to any structure that supports a moving platform on a base.

The term "platform" as used herein refers to any structure that comprises one or more fixed components and provides support for or positioning of a surgical instrument. The "platform" may form a 2D plane or may be of any 3-dimensional structure.

The term "open rectangular" as used herein refers to any rectangular that is not closed. It may include at least 3 sides or 4 sides of a rectangular.

One of ordinary skill in the art can appreciate that the base further defines the base plane. For example, with reference to FIG. 2, in one embodiment, a miniature parallel manipulator robot may have an open half-plane, such as an open rectangular base 1 that defines a base plane. The robot may have a moving platform 6 that is of a shape of a half circle and a cross bar 15 that together define a 2D plane. The robot may have at least three legs A, B and C to support the moving platform 6 on the base 1. In one embodiment, the moving platform may additionally have a surgical arm that has a guide 8 attached thereto at an end for holding a surgical instrument 9. In one embodiment, the guide may be a hollow cylinder that allows the surgical instrument to pass through. Alternatively, the hollow cylinder guide may be directly attached to the moving platform of the robot.

In one embodiment, each leg may have two parts: the lower part 12 and the upper part 4, and three joints: universal joint 3, prismatic joint 13, and spherical joint 5. The lower part 12 and the upper part 4 may be rotatably joined via a prismatic joint 13 with an actuator, such as a linear actuator. The linear actuator may control the upper part of the leg so that it slides linearly relative to the lower part of the leg. Additionally, the upper part of the leg may also slide and rotate simultaneously or independently relative to the lower part of the leg. The lower part of the leg may be joined to the base and the upper part of the leg joined to the moving platform. In one embodiment, a rotary actuator 2 may be attached to a fixed point on the base 1, with the shaft of the rotary actuator being attached to the lower part of the leg through a passive revolute joint or universal joint 3. Since the rotary actuators are resting on the fixed base structure, higher accelerations are available due to the smaller inertial effects. The passive revolute joint that joins the lower part of the leg and the shaft of the rotary actuator may provide a 1-degree-of-freedom (DOF) movement. In one embodiment, the upper part of the leg 4 may be connected to the moving platform 6 via a spherical joint 5, which provides a 3-DOF movement. All the three legs A, B and C may be joined between the base and the moving platform in the same manner.

The legs may be configured non-symmetrically on the base and moving platforms. For example, on the base 1, two rotary actuators for attaching two legs may be placed on each corner of the opening rectangular and the third rotary actuator for attaching the third leg may be placed on the longitudinal or longest side of the opening rectangular and equally spaced between the other two fixed points. In another example, on the moving platform 6, the three spherical joints for attaching the three legs may be placed equally in space, with one placed on each end of the half circle, and the third joint placed in the middle of the arc of the half circle. This configuration makes a frontally wide open architecture that enables the mechanism to embrace and manipulate column-shape objects and minimize interferences with kinetic chains of the robot.

Figure 2:
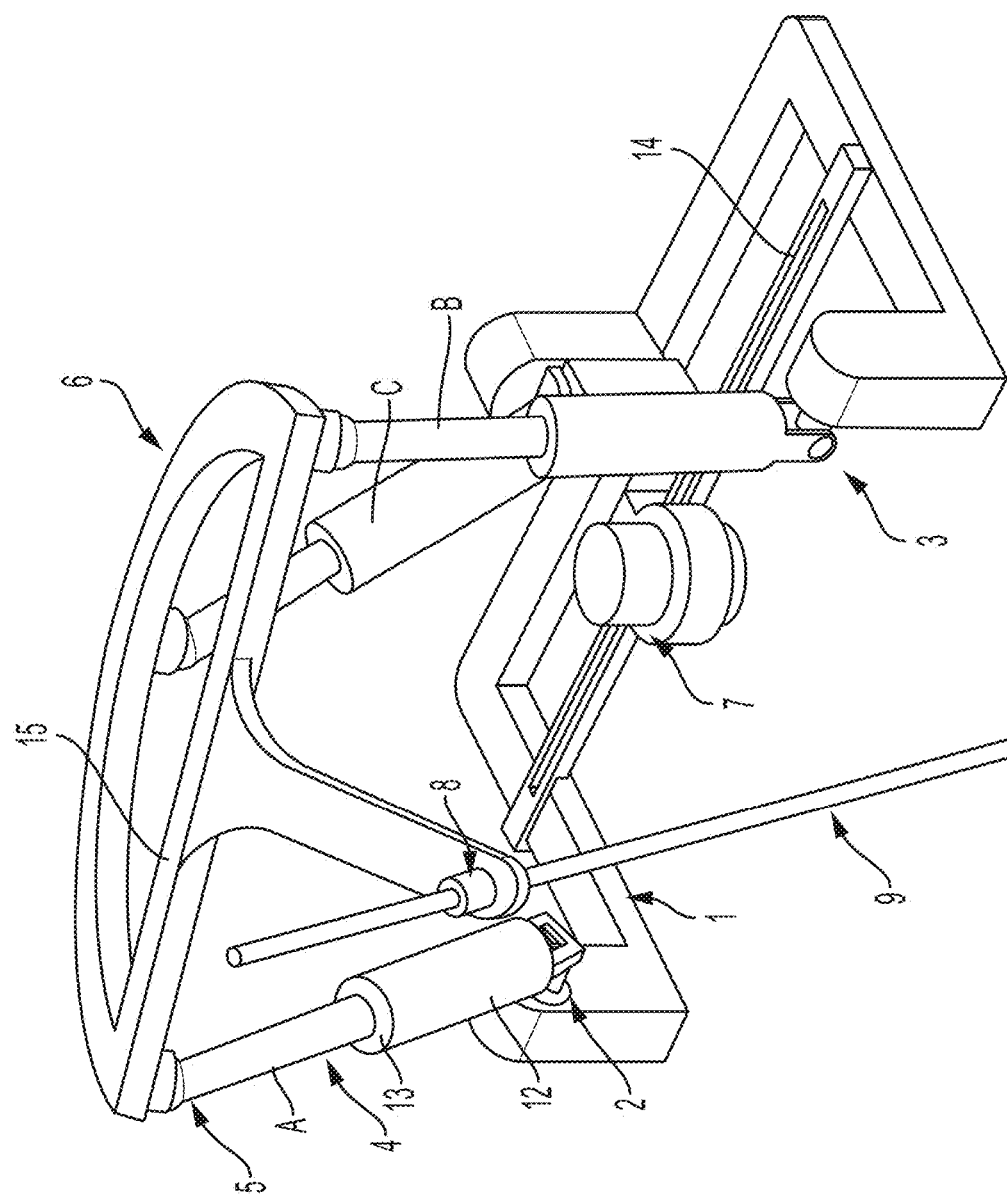
FIG. 2 illustrates an example of a robot for spine surgery according to one embodiment.

With further reference to FIG. 2, in one embodiment, the robot may additionally include an imaging sensor 7, such as an ultrasonic imaging sensor, mounted thereon. The imaging sensor may be installed on a housing that is movably fixed to a tracking system 14, and can move along the track longitudinally. Alternatively and/or additionally, the tracking system 14 may also move laterally along the short sides of the open rectangular base 1.

Figure 3:
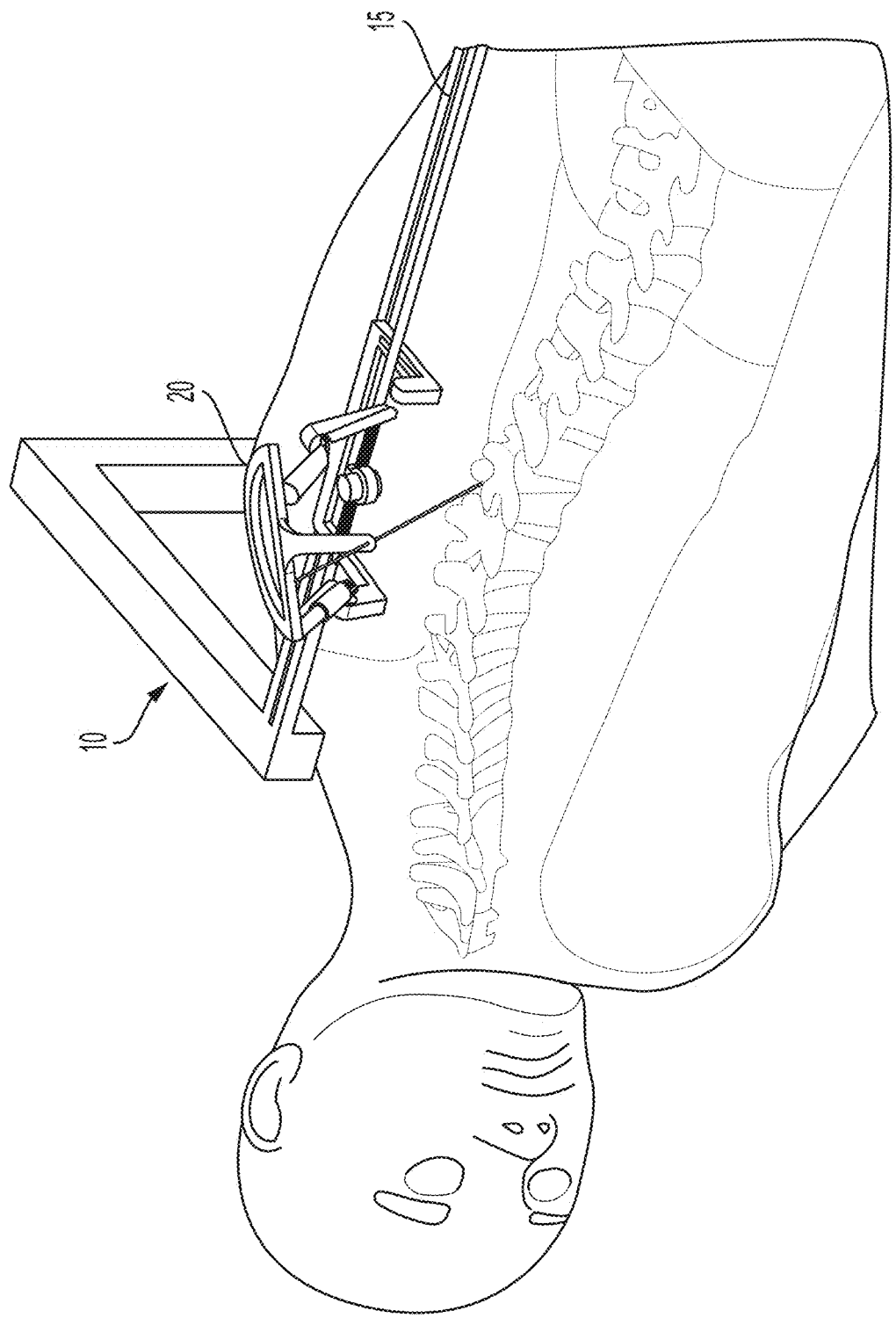
FIG. 3 illustrates a schematic of a surgical robot for spinal interventions according to one embodiment.

With reference to FIG. 3, in one embodiment in the context of spine surgery, the robot system 20 can be movably fixed to a structure 10 and configured to move along a track 15 of the structure to reach different sections along the spine. In one embodiment, the longest side of the rectangular base can be movably fixed to a rail of the track 15. The movement of the robot system 20 on the track 15 can be manual or motor-driven. Once the robot 20 is moved to a section of the spine, it can be electronically controlled such that the surgical instrument that passes through the hollow cylinder on the moving platform can be precisely positioned.

In one embodiment, the rotary actuator and the linear actuator installed on each leg can be used to electronically actuate each leg. This will allow the 6-DOF movement of the top platform in the 3D space to accurately position a surgical instrument such as a screw. In one embodiment, the robot can move and rotate along the x, y, and z axes. The precision of the locomotion and rotation of the robot can be 1 mm and 1 degree, respectively, or higher, which are permissible to ensure satisfactory screw implantation.

The robot system can be constructed in various configurations and sizes. For example, the base may be a semi-rectangular fixed platform having the dimensions 75 cm×50 cm. In another embodiment, the semi-rectanglar fixed platform has the dimension of 50 cm×25 cm, preferably 30 cm by 15 and more preferably 15 cm by 7.5 cm. In another embodiment the moving platform may be of a semi-circle frame with a radius of 20, 15, 10, 5, 6, or 3 cm. In one embodiment, the radius of such platform is 6 cm. In one embodiment, the material for the frames of the base and moving top platform can be either stainless steel or aluminum alloys. In one embodiment, the minimum length of the linear actuators can be around 10 cm and the maximum length of the linear actuators can be around 20 cm. In one embodiment, the upper part and lower part of each leg may be part of the linear actuator, thus, the minimum and maximum lengths of the linear actuators may represent the minimum and maximum distances between the moving top platform and the base, respectively. In another embodiment, the range of the linear actuators may vary (increase or decrease) by up to 50%. In one embodiment, the rotary actuator may use a stepper motor or a servo motor with a nominal torque of 0.05 to 0.5 N·m followed by a low-ratio gearbox, with a backlash less than 0.1°, to enlarge the shaft torque. In one embodiment, the linear actuation at each leg may use a ball screw system powered by a stepper motor or a servo motor with a nominal torque of 0.01 to 0.1 N·m.

Figure 4:
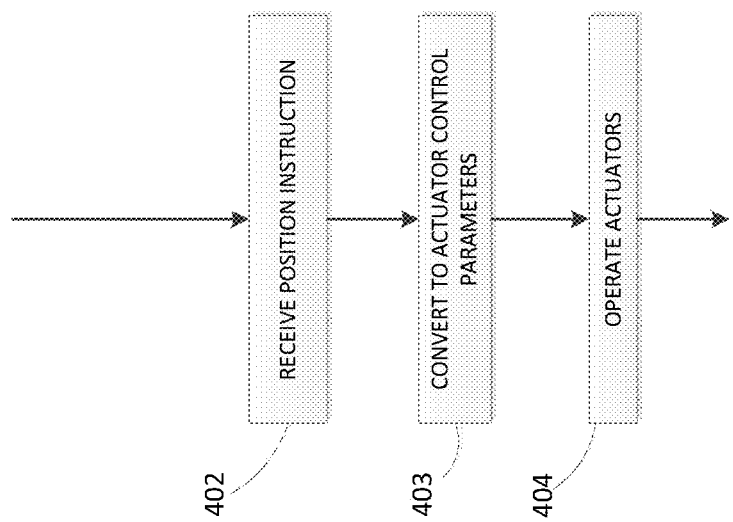
FIG. 4 illustrates a control panel for the system to receive position instruction from user according to one embodiment.

With reference to FIG. 4, the precision control of the movement of the platform is further explained. Each of the actuators may require one or more control parameters in order to operate. The robot system may be configured to receive the control parameters from a microprocessor or a computer. The microprocessor may be configured to receive trajectory position instructions 402, convert the position instructions to one or more actuator control parameters 403 and send the one or more control parameters to the one or more actuators via electrical signals. In one embodiment, the microprocessor may implement computer-readable program instructions (e.g. C, C++, Matlab, or any other computer languages) to convert desired trajectory position instructions to actuator control parameters. The trajectory position instruction may include a multitude of values, such as x, y, z positions, alpha, beta, theta angles, steps and time intervals etc. (shown in FIG. 5). Translational and rotational increments can be adjusted by "Delta Trn" and "Delta Rot" buttons, respectively. For instance, "Delta Trn" may range from 1 to 10 (mm), while "Delta Rot" may range from 0.1 to 1 (deg). "Sample time" ranges between 0.001 and 0.01 (s), and "Time interval" from 1 to 10 (s). "Step ratio" is dependent to the driver adjustments and may range from 1 to 250. The actuator control parameters may include the values for displacements and rotations of each actuator.

In one embodiment, the microprocessor may convert the position instruction to one or more control parameters associated with one or more actuators, either linear actuators or rotary actuators. In one embodiment, in order to reduce the computing time, the microprocessor may optimize the conversion by checking whether the position instruction will trigger the actuation of only a few of all of the actuators. For example, if a new position involves only the moving top platform to raise up (i.e. a translation of z), then the microprocessor may determine that only the linear actuators joining the upper and lower parts of the legs need to be actuated whereas the rotary actuators remain the same. Accordingly, the microprocessor may determine to compute only the new control parameters of the linear actuators, and consequently, send the new control parameters only to the linear actuators.

Figure 5:
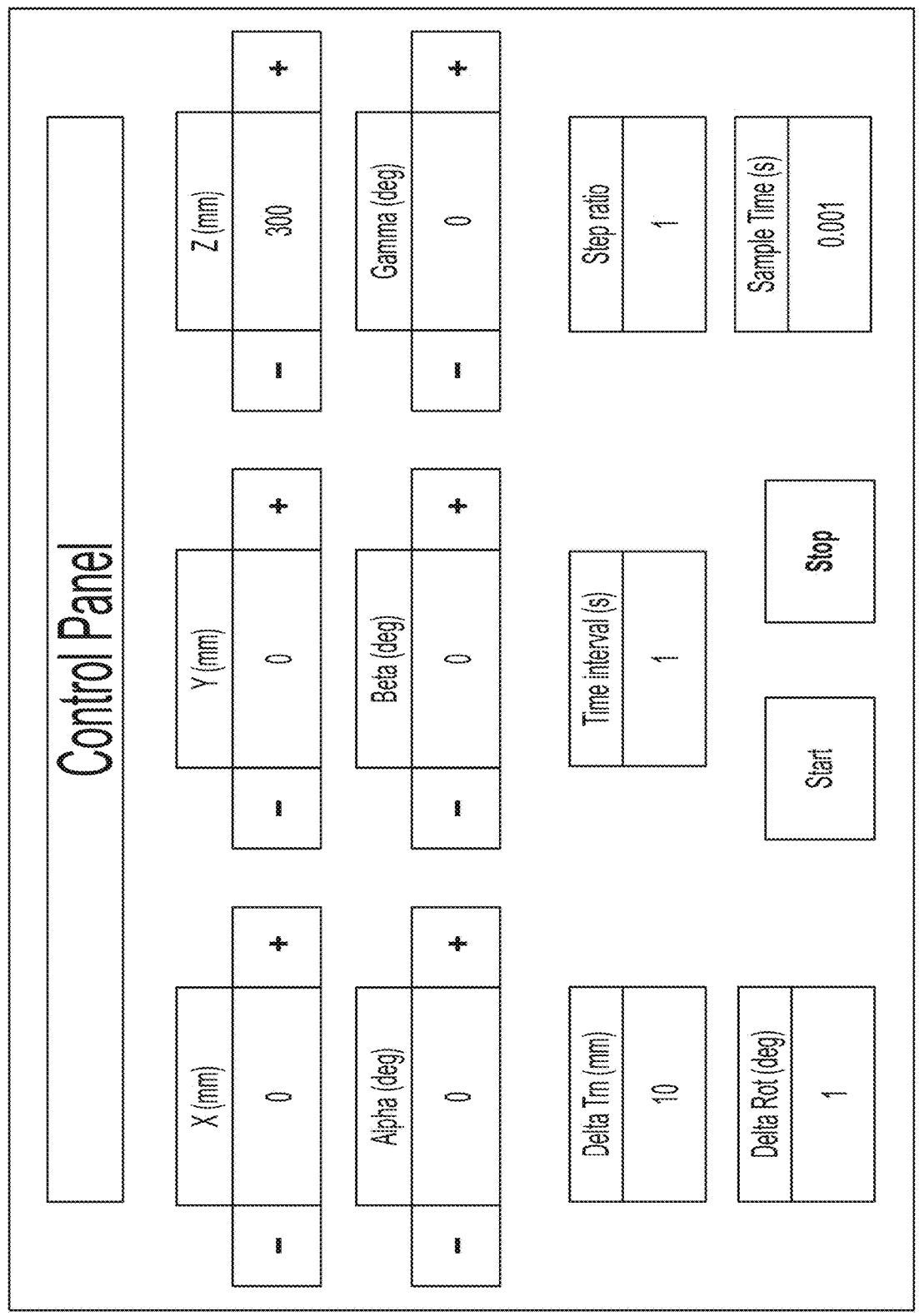
FIG. 5 illustrates a diagram of actuator control for operation of the surgical robot according to one embodiment.

The robot system can be controlled from a user (surgeon) manually or autonomously by receiving the position instruction in various ways. With reference to FIG. 5, in one embodiment, the system may receive position instruction from a user via a control panel, such as a touch screen control panel. Alternatively and/or additionally, the system may receive a command from a 6-DOF joystick that is connected to the system and operated by the user. In another embodiment, or additionally, the system may act as a slave robot and receive commands from a master robot. The master robot is a miniature version of the robot system, communicatively coupled wired or wirelessly to the slave robot, and is under the control of a surgeon. As the master robot is moved by the surgeon, the slave robot receives from the master robot the movement of the master robot and copies the movements with more precision and higher force. Various implementations of the master robot and slave robot may be implemented. For example, the master device and the slave device may be integrated in an operating room or may be separately arranged. A workstation may be used for the surgeon to command the slave robot. The workstation may include a master robot and a visual aid, e.g. a monitor, for the surgeon to see the image of the spine or bone. Master robot may be a joystick or a miniature version of the slave robot. The workstation may be located inside the operating room, or outside the operating room, which is called remote control or teleoperation. In another embodiment, the robot may also receive position instructions based on a path planning developed from a preoperative procedure, as will be described as below.

Figure 6:
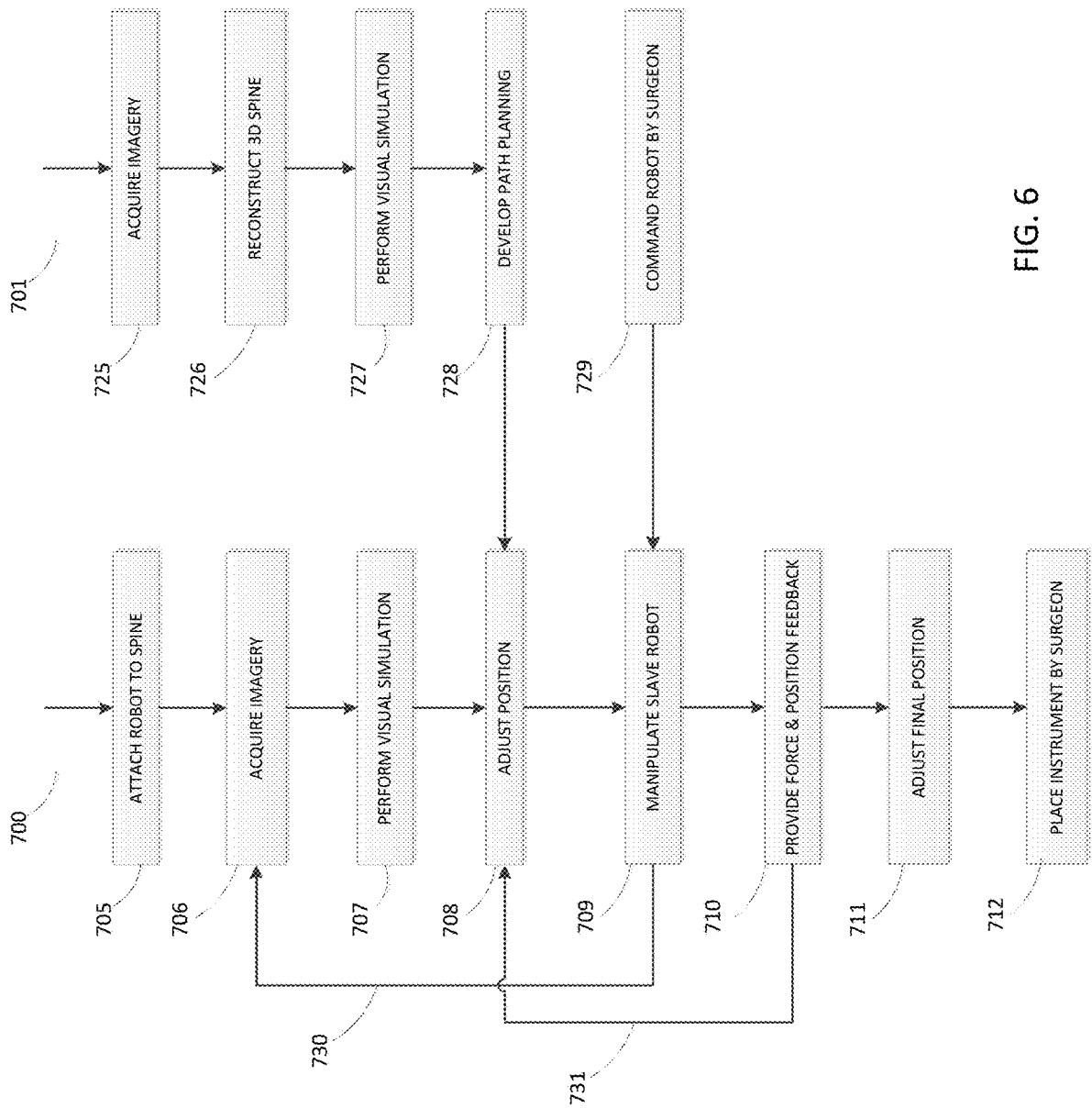
FIG. 6 illustrates a diagram of surgical procedure using the surgical robot according to one embodiment.

With reference to FIG. 6, an intraoperative planning and preoperative planning in using the robot system disclosed in this document are explained. By way of examples, spine surgery is ideally suited for the integration of robotic-assisted surgical procedures. The advancement of training of spine surgeons and the integration of image guidance with precise intraoperative imaging, computer- and robot-assisted treatment modalities constitute the era of reducing treatment morbidity in spinal surgery. The application of image-guided robotic assistance to spinal procedures enables surgeons to visualize and navigate complex anatomic structures during the planning and execution stages. These platforms provide critical support for minimally invasive surgical procedures while simultaneously improving their accuracy and lowering the incidence of neurological deficits.

In one embodiment, the preoperative planning 701 may include the steps of acquiring imagery 725 using an imaging capturing device (such as X-ray, ultrasound imaging and/or MRI or the imaging probe onboard the robot system), reconstructing a 3D spine based on the captured imagery, where the 3D reconstruction allows a surgeon to be able to perform a visual simulation 727 on the spine and develop a path planning 728 based on the study of spine structure from the visual simulation. The developed path planning can be used in the intraoperative planning process 700.

With further reference to FIG. 6, in one embodiment, the intraoperative planning process 700 may include attaching the robot system to the spine on which surgery is to be performed (see FIG. 3), acquiring imagery 706 using an imaging probe such as an ultrasound imaging onboard the robot system, and performing visual simulation of the spine structure based on the captured imagery 707. Based on the result of the visual simulation, the surgeon may provide position instructions to the robot 708 and manipulate the robot 709. Additionally, the process of acquiring imagery 706, performing visual simulation 707 and providing position instructions to the robot 708 may repeat 730 after the robot is manipulated so that the position of the robot can be adjusted.

The ways for a surgeon to provide position instruction to the robot system, as disclosed above in this document, may include using a control panel to enter the trajectory positions, angles or other parameters required to control one or more actuators of the robot, or using a joystick device, or using the 6-DOF robot system as a slave robot and controlling a master robot system 729 to manipulate the slave robot 709 to achieve high precision. In an alternative embodiment, or additionally, the surgeon may use the path planning 728 that was developed in the preoperative planning process 701. For example, according to a preoperatively planned trajectory, the robot guides the moving hollow cylinder to the correct position for the surgeon to drill. Once the system reaches a final position 711 based on the planned trajectory, the surgeon may place the instrument into the body 712, such as drill or insert a screw into the spine.

With further reference to FIG. 6, the intraoperative planning 700 may further include providing force and position feedback 710. Based on the feedback of force and position 731, the robot system may readjust the position 708 and reach a final position 711.

Figure 7:
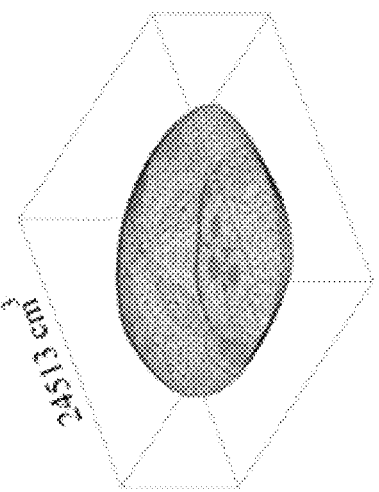
FIG. 7 illustrates a reachable workspace of the surgical robot according to one embodiment.

With the 6-DOF movement, the robot system disclosed in this document may reach a wide range of workspace. With reference to FIG. 7, different performance indices, such as manipulability, dexterity, translational sensitivity, and rotational sensitivity on the plate Z=0.3 (m) can be calculated. In one embodiment, when g=1 (m) and h=0.5 (m), where g and h are the radii of the fixed and moving platforms, respectively, and assuming a cubic with 1 (m) length, 1 (m) width and 1 (m) height located 0.25 (m) above the base platform, the reachable workspace that is constructed by the intersection of 3 spheres (corresponding to 3 legs) can reach about 24,513 cubic centimeters.

The above-disclosed features and functions, as well as alternatives, may be combined into many other different systems or applications. Various components may be implemented in hardware or software or embedded software. Various presently unforeseen or unanticipated alternatives, modifications, variations or improvements may be made by those skilled in the art, each of which is also intended to be encompassed by the disclosed embodiments.

The invention claimed is:

1. A robot for use in a spinal surgery, the robot comprising:
    an open rectangular base comprising at least three sides of which the longest side is configured to slide on a rail of a fixed support;
    a moving top platform comprising a portion of a circle having two ends, a cross bar connecting the two ends, and a guide attached to the cross bar and configured to attach a surgical instrument thereon; and
    three legs configured to support the top platform on the base and move the top platform in 6-degree-of-freedom relative to the base;
    wherein:
        each of the three legs comprises a lower part and an upper part rotatably joined by an electric linear actuator, the linear actuator being configured to slide the upper part linearly relative to the lower part,
        the lower part of each leg is joined to a shaft of a rotary actuator through a passive resolute joint, wherein the rotary actuator is mounted on the base at a fixed point and the shaft of the rotatory is configured to rotate relative to the base, and
        the upper part of each leg is joined to the top platform at a fixed point via a passive spherical joint.

2. The robot of claim 1, wherein the guide of the top platform is a hollow cylinder.

3. The robot of claim 1, wherein the three rotary actuators are equally spaced with respect to each other.

4. The robot of claim 1, wherein the three passive spherical joints are equally spaced with respect to each other.

5. The robot of claim 1, wherein the base is movably mounted to the rail of a tracking system and configured to slide longitudinally or laterally relative to the tracking system.

6. The robot of claim 1, wherein the base comprises a housing for an imaging probe wherein the housing is configured to slide longitudinally or laterally relative to the base.

7. The robot of claim 6, wherein the imaging probe is an ultrasound probe.

8. The robot of claim 1, wherein each of the rotary actuators is configured to rotate using servo or stepper motor.

9. The robot of claim 1, wherein each of the rotary actuators comprises a needle roller bearing.

10. A method for controlling a robot according to claim 1 for use in a spinal surgery, comprising the steps of:
    receiving, using a microcontroller, a trajectory position instruction;
    generating, using a microcontroller, one or more control parameters for each of the three rotary actuators and three linear actuators based on the position instruction;
    operating, using a microcontroller, at least one of the three rotary actuators and three linear actuators based on at least one or the one or more control parameters.

11. The method of claim 10, wherein the robot is communicatively coupled to a master robot, and wherein the method further comprises receiving, using a microcontroller, one or more position instructions from the master robot.

12. The method of claim 10, wherein receiving the position instruction comprises receiving, via a microprocessor, a user command via a graphical user interface.

13. The method of claim 10, wherein the robot is communicatively coupled to a joystick device, and wherein receiving the position instruction comprises receiving, via a microprocessor, a position instruction via the joystick device.

14. The method of claim 10, wherein receiving the position instruction comprises receiving, via a microprocessor, a position instruction via a path planning.

15. The method of claim 14, wherein the path planning is developed in a preoperative planning process.

16. The method of claim 10, wherein generating the set of control parameters for actuators comprises adjusting, by a microprocessor, the position based on a force or position feedback.

* * * * *